(12) United States Patent
Roorda

(10) Patent No.: US 10,792,481 B2
(45) Date of Patent: *Oct. 6, 2020

(54) IMPLANTABLE DRUG DELIVERY DEVICE

(71) Applicant: Nano Precision Medical, Inc., Emeryville, CA (US)

(72) Inventor: Wouter Erik Roorda, Emeryville, CA (US)

(73) Assignee: NANO PRECISION MEDICAL, INC., Emeryville, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/133,410

(22) Filed: Sep. 17, 2018

(65) Prior Publication Data

US 2019/0015647 A1 Jan. 17, 2019

Related U.S. Application Data

(63) Continuation of application No. 15/337,115, filed on Oct. 28, 2016, now Pat. No. 10,105,523, which is a continuation of application No. 15/093,472, filed on Apr. 7, 2016, now Pat. No. 9,511,212, which is a continuation of application No. PCT/US2015/063940, filed on Dec. 4, 2015.

(60) Provisional application No. 62/155,464, filed on Apr. 30, 2015, provisional application No. 62/088,646, filed on Dec. 7, 2014.

(51) Int. Cl.
| | |
|---|---|
| A61M 31/00 | (2006.01) |
| A61M 5/142 | (2006.01) |
| A61M 37/00 | (2006.01) |
| A61K 9/20 | (2006.01) |
| A61K 9/00 | (2006.01) |
| A61K 9/48 | (2006.01) |
| A61K 38/22 | (2006.01) |

(52) U.S. Cl.
CPC ......... *A61M 31/002* (2013.01); *A61K 9/0004* (2013.01); *A61K 9/20* (2013.01); *A61K 9/4808* (2013.01); *A61K 38/2278* (2013.01); *A61M 5/14276* (2013.01); *A61M 37/0069* (2013.01); *A61M 2202/06* (2013.01)

(58) Field of Classification Search
CPC ............ A61M 31/002; A61M 5/14276; A61K 9/0004
USPC ...................................... 604/892.1
See application file for complete search history.

(56) References Cited

U.S. PATENT DOCUMENTS

| | | | |
|---|---|---|---|
| 4,054,138 A * | 10/1977 | Bucalo ................. | A61K 9/0024 424/426 |
| 9,511,212 B2 * | 12/2016 | Roorda ............... | A61M 31/002 |
| 2005/0096296 A1 | 5/2005 | Fikstad | |
| 2006/0067980 A1 | 3/2006 | Hennessy et al. | |
| 2010/0158980 A1 | 6/2010 | Kopczynski et al. | |

(Continued)

*Primary Examiner* — Rebecca E Eisenberg
*Assistant Examiner* — Anh Bui
(74) *Attorney, Agent, or Firm* — Kilpatrick Townsend & Stockton LLP; Wouter Roorda

(57) ABSTRACT

The invention pertains to implantable medical devices for controlled delivery of therapeutic agents. Some devices according to the invention have a titanium reservoir, and a porous titanium oxide based membrane to control the rate of release of the therapeutic agent. The reservoir contains a formulation of the active agent, and means to promote water uptake into the reservoir upon implantation. In some embodiments the means include a gas with a higher solubility in than air water.

16 Claims, 4 Drawing Sheets

(56) References Cited

U.S. PATENT DOCUMENTS

| | | | |
|---|---|---|---|
| 2011/0106006 A1* | 5/2011 | Martin | A61K 47/34 604/93.01 |
| 2011/0223233 A1 | 9/2011 | Martin et al. | |
| 2012/0089121 A1 | 4/2012 | Lee et al. | |
| 2014/0336593 A1* | 11/2014 | Coppeta | A61F 9/0017 604/244 |
| 2015/0057227 A1* | 2/2015 | Leung | A61K 38/26 514/11.7 |

\* cited by examiner

IMPLANTABLE DRUG DELIVERY DEVICE

CROSS-REFERENCES TO RELATED APPLICATIONS

The present application is a continuation of U.S. patent application Ser. No. 15/337,115, filed Oct. 28, 2016 (Allowed); which is a continuation of U.S. patent application Ser. No. 15/093,472 filed Apr. 7, 2016, which issued as U.S. Pat. No. 9,511,212; which is a continuation of International Patent Application No. PCT/US2015/063940, filed Dec. 4, 2015; which claims priority to U.S. Provisional Patent Application Nos. 62/155,464 filed Apr. 30, 2015, and 62/088,646 filed Dec. 7, 2014; the teachings of all of which are hereby incorporated by reference in their entireties for all purposes.

BACKGROUND OF THE INVENTION

Many beneficial substances, including many therapeutic agents, require long-term delivery to a target site of action to be optimally effective. Well-known examples include drugs that need to be administered for extended periods of time to a patient. Many extended release formulations have been developed for this purpose. A common issue with all of these formulations is that the drugs administered need to be stabilized in the formulation for the duration of the shelf-life of their dosage form, in addition to the stabilization required during the extended release period.

In many cases, drugs are more stable in a dry or solid formulation than in a dissolved state, hence formulations having a solid formulation during shelf life are often preferred. In some instances, the solid drug may be dispersed in a liquid, resulting in a liquid formulation comprising a solid drug.

However, in order to be released from their dosage form, drugs almost always rely on some type of diffusional mechanism, which inherently requires the drugs to be in solution. Therefore, many dosage forms rely on the uptake of water after administration to a patient to bring the drugs from a solid form into solution, prior to release from the dosage form.

One type of dosage form that has been developed to address the issue of extended release of therapeutic agents is that of implantable drug delivery devices, in which a reservoir holding a drug formulation is combined with a release rate controlling mechanism, such as a release rate controlling membrane. In many instances, when a solid or dry formulation, like a powder, is filled into such a reservoir, a quantity of air is included in the reservoir. As was mentioned above, many of these dosage forms rely on the uptake of water to bring their drugs from the solid form into solution, essentially requiring that air inside the reservoir be replaced with water. Oftentimes, this will require simultaneous mass transport of water into a device and air out of the device. For those dosage forms that do not allow for such simultaneous transport, proper hydration of the formulation inside the reservoir may be impeded. One type of dosage form where this can be the case is implantable drug delivery systems having a capsule encapsulating a reservoir containing a therapeutic agent in a dry form, and a release rate controlling membrane based on nanopores. In many cases, the reservoir and the nanopores will contain an amount of air in addition to the therapeutic agent, and mass transport of interstitial fluid into the reservoir after implantation may be impeded by the presence of the air. Therefore, additional technologies are desired that allow for proper hydration in such dosage forms.

BRIEF SUMMARY OF THE INVENTION

In one embodiment, the present invention provides an implantable drug delivery device, the device comprising:
   a capsule suitable for implantation;
   a reservoir encapsulated by the capsule;
   at least one nanoporous membrane in fluid contact with the reservoir;
   a therapeutic agent;
   and a quantity of gas, wherein the therapeutic agent and the quantity of gas are contained within the reservoir, and wherein the quantity of gas comprises one or more gases with a solubility in water at a temperature of 37° C. and a pressure of 1 atmosphere that is greater than the solubility of air in water at a temperature of 37° C. and a pressure of 1 atmosphere.

In certain aspects, the quantity of gas comprises at least 10%, 25%, 50%, or 90% by weight of one or more gases with a solubility in water of more than 22 mg/liter at a temperature of 37° C. and a pressure of 1 atmosphere.

In certain aspects, the implantable drug delivery device of claim 1, wherein the quantity of gas comprises a substantially pure gas with a solubility in water of more than 22 mg/liter at a temperature of 37° C. and a pressure of 1 atmosphere.

In certain instances, the at least one gas with a solubility in water of more than 22 mg/liter is $CO_2$, $N_2O$ or Ar.

In certain instances, the device comprises a cap located on the capsule over the nanoporous membrane, such as wherein the cap forms a substantially hermetical seal over the nanoporous membrane. The cap can be one of a biodegradable cap or a soluble cap.

In certain instances, the at least one nanoporous membrane is a titania nanotube membrane, optionally configured to achieve extended release of the therapeutic agent.

In another embodiment, the present invention provides a system for extended release of a therapeutic agent, comprising
   an implantable drug delivery device having a capsule suitable for implantation, having a reservoir encapsulated by the capsule, and having at least one nanoporous membrane in fluid contact with the reservoir, the reservoir containing the therapeutic agent and containing a first quantity of gas; and
   a packaging system having a substantially gas-impermeable barrier shell surrounding an interior, the interior containing a second quantity of gas,
wherein the first quantity of gas and the second quantity of gas each comprise at least 10% by weight of one or more gases with a solubility in water of more than 22 mg/liter at a temperature of 37° C. and a pressure of 1 atmosphere.

In another embodiment, the present invention provides a system for extended release of a therapeutic agent, comprising
   an implantable drug delivery device having a capsule suitable for implantation, having a reservoir encapsulated by the capsule, and having at least one nanoporous membrane in fluid contact with the reservoir, the reservoir containing the therapeutic agent and containing a first quantity of gas; and
   a hollow implantation needle having a sharpened distal end and having a lumen, the lumen containing the drug delivery device and containing a second quantity of gas in fluid contact with the nanoporous membrane;

wherein the first quantity of gas and the second quantity of gas each comprise at least 10% by weight of one or more gases with a solubility in water of more than 22 mg/liter at a temperature of 37° C. and a pressure of 1 atmosphere.

In certain aspects, the system further comprises a removable cap located over the sharpened distal end of the hollow implantation needle. In certain aspects, the removable cap forms a substantially hermetical seal over the needle.

In certain aspects, the drug delivery device is oriented with the at least one nanoporous membrane in a proximal direction.

In another embodiment, the present invention provides a system for extended release of a therapeutic agent, comprising an implantable drug delivery device having a capsule suitable for implantation, having a reservoir encapsulated by the capsule, and having at least one nanoporous membrane in fluid contact with the reservoir, the reservoir containing the therapeutic agent and containing a first quantity of gas; and a hollow implantation needle having a sharpened distal end and having a lumen, the lumen containing the drug delivery device, containing a moveable plug located distally to the drug delivery device and containing a second quantity of gas located between the drug delivery device and the moveable plug;

wherein the first quantity of gas and the second quantity of gas each comprise at least 10% by weight of one or more gases with a solubility in water of more than 22 mg/liter at a temperature of 37° C. and a pressure of 1 atmosphere.

In certain aspects, the plug is one of a soluble plug and a biodegradable plug. For example, the plug forms a substantially hermetical seal in the needle.

In certain aspects, at least one of the first quantity of gas and the second quantity of gas comprise at least 25%, 50%, or 90% by weight of one or more gases with a solubility in water of more than 22 mg/liter at a temperature of 37° C. and a pressure of 1 atmosphere.

In certain aspects, at least one of the first quantity of gas and the second quantity of gas comprises a substantially pure gas with a solubility in water of more than 22 mg/liter at a temperature of 37° C. and a pressure of 1 atmosphere.

In certain aspects, at least one gas with a solubility in water of more than 22 mg/liter at a temperature of 37° C. and a pressure of 1 atmosphere is one of $CO_2$, $N_2O$ and Ar.

In certain aspects, the at least one nanoporous membrane is a titania nanotube membrane.

In certain aspects, the at least one nanoporous membrane is configured to achieve extended release of the therapeutic agent.

In yet another embodiment, the present invention provides an implantable drug delivery device, the implantable drug delivery device comprising:

a capsule suitable for implantation;
a reservoir encapsulated by the capsule; at least one nanoporous membrane in fluid contact with the reservoir;
a therapeutic agent; and means to promote uptake of interstitial fluid into the reservoir upon implantation of the drug delivery device into a subject, the therapeutic agent and means to promote uptake of interstitial fluid into the reservoir upon implantation of the drug delivery device into the subject being contained within the reservoir.

In certain aspects, the means to promote uptake of interstitial fluid into the reservoir upon implantation of the drug delivery device into a subject comprises a quantity of gas, wherein the quantity of gas comprises at least 10%, 25%, 50%, or 90% by weight of one or more gases with a solubility in water of more than 22 mg/liter at a temperature of 37° C. and a pressure of 1 atmosphere.

In certain aspects, the means to promote uptake of interstitial fluid into the reservoir upon implantation of the drug delivery device into a subject comprises a substantially pure gas with a solubility in water of more than 22 mg/liter at a temperature of 37° C. and a pressure of 1 atmosphere.

In certain aspects, the gas with a solubility in water of more than 22 mg/liter at a temperature of 37° C. and a pressure of 1 atmosphere is one or more of $CO_2$, $N_2O$ and Ar.

In certain aspects, the at least one nanoporous membrane is a titania nanotube membrane.

In certain aspects, the at least one nanoporous membrane is configured to achieve extended release of the therapeutic agent.

In certain aspects, the means to promote uptake of interstitial fluid into the reservoir upon implantation of the drug delivery device into a subject comprises a quantity of a solid acid and a quantity of a solid salt of carbonic acid.

In certain aspects, the quantity of the solid acid and the quantity of the solid salt of carbonic acid are each less than 10% by weight of the quantity of the therapeutic agent.

In still yet another embodiment, the present invention provides an implantable drug delivery device comprising:

a capsule suitable for implantation;
a reservoir encapsulated by the capsule; and
at least one nanoporous membrane in fluid contact with the reservoir;

the reservoir containing a therapeutic agent, a quantity of a solid acid and a quantity of a solid salt of carbonic acid.

In certain aspects, the quantity of the solid acid and the quantity of the solid salt of carbonic acid are each less than 10% by weight of the quantity of the therapeutic agent.

In certain aspects, the therapeutic agent is a protein or peptide such as beta-glucocerobrosidase, interferon alpha, interferon beta, agasidase alpha, agasidase beta, exenatide, octreotide, LHRH, LHRH analog, calcitonin, nutropin/somatropin, factor VIII, aldesleukin, forigerimod, NP fusion proteins, IL-12, a melanocyte stimulating hormone, and bapineuzumab. The therapeutic agent is can be exenatide or octreotide.

In another embodiment, the present invention provides a solid pharmaceutical composition, the composition comprising:

a therapeutic agent; and at least one humectant, wherein the at least one humectant is a water-soluble gas having a solubility in water at a temperature of 37° C. and a pressure of 1 atmosphere that is greater than the solubility of air in water at a temperature of 37° C. and a pressure of 1 atmosphere.

In certain aspects, the water-soluble gas has a solubility which is or than 22 mg/liter at a temperature of 37° C. and a pressure of 1 atmosphere.

In certain aspects, the water-soluble gas is a member selected from the group consisting of $CO_2$, $N_2O$ and Ar.

In certain aspects, the weight ratio of therapeutic agent to the at least one humectant is between 1 part of the therapeutic agent to 99 parts of the humectant and 99 parts of the therapeutic agent and 1 part of the at least one humectant.

In certain aspects, the weight ratio of the therapeutic agent to the at least one humectant is between 20 part of the therapeutic agent to 80 parts of the at least one humectant and 80 parts of the therapeutic agent and 20 part of the at least one humectant.

In certain aspects, the composition is contained within a reservoir of an implantable drug delivery device, the device having a capsule suitable for implantation, the capsule encapsulating the reservoir, and the device having at least one nanoporous membrane in fluid contact with the reservoir.

In still yet another embodiment, the present invention provides method for increasing the rate of hydration of a solid pharmaceutical composition in an encapsulated environment of an implantable capsule, the method comprising: providing a solid pharmaceutical composition having a humecant, wherein the humecant increases the solubility of the encapsulated environment relative to air to thereby increase the rate of hydration of the solid pharmaceutical composition.

In still yet another embodiment, the present invention provides a method for increasing the uptake of interstitial fluid in an implantable device having an encapsulated environment, the method comprising: providing a solid pharmaceutical composition having a humectant, wherein the humectant increases the solubility of the encapsulated environment relative to air to thereby increase the rate of interstitial fluid uptake of the implanted device.

These and other aspects, objects and advantages will become more apparent when read with the detailed description and the figures that follow.

DEFINITIONS

Figure 1:
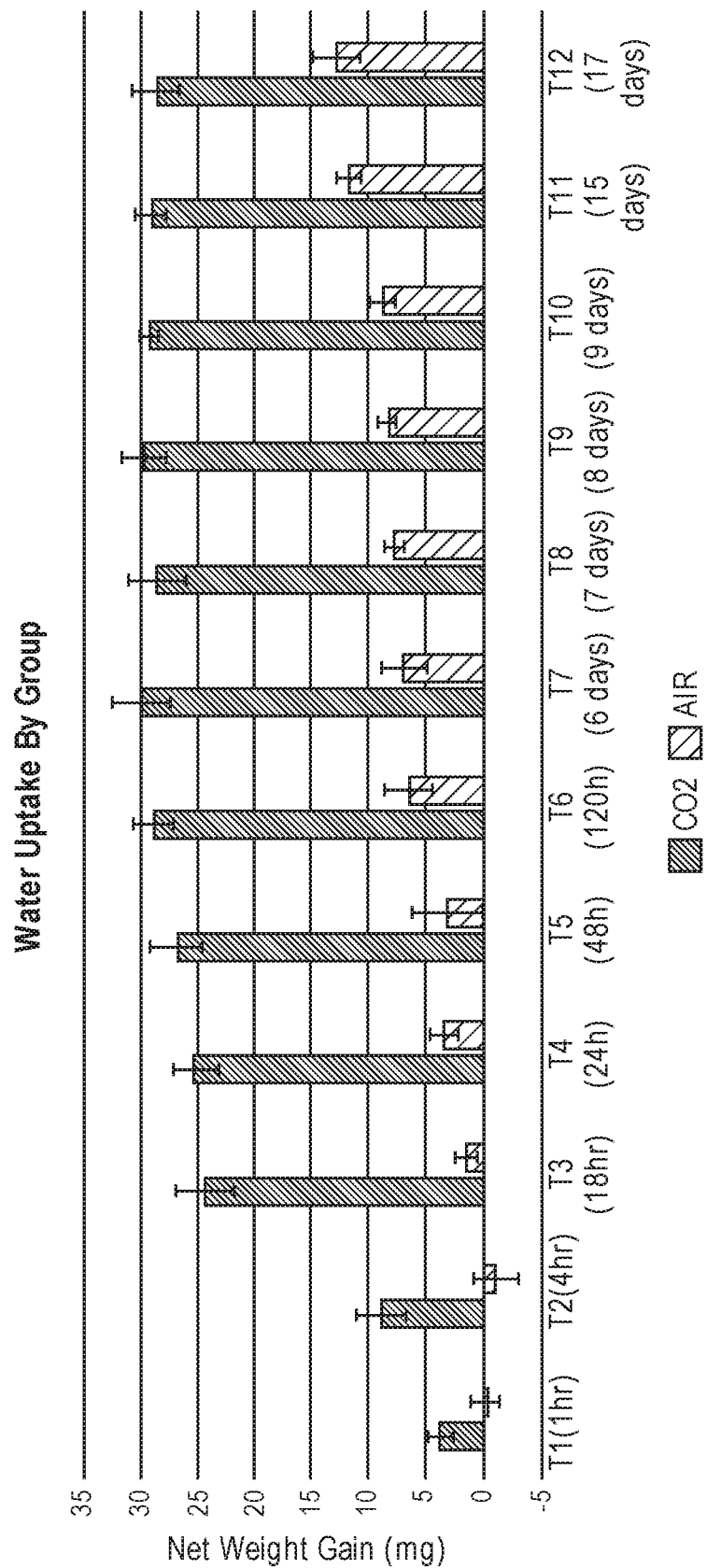
FIG. 1 illustrates the effect of an atmosphere of $CO_2$ vs. an atmosphere of air in the reservoir of a device on the rate of water uptake in the device after immersion in a water bath.

"Therapeutic agent" refers to any agent capable of providing a therapeutic response, such as a drug or biologic.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full length proteins, wherein the amino acid residues are linked by covalent peptide bonds.

"Membrane" refers to a porous structure allowing mass transport of molecules from one side of the structure to the other through the structure.

"Nanoporous membrane" refers to a porous structure wherein at least some of its pores are open on both ends and form fluid-filled pathways having a smallest dimension less than one micrometer and allowing for mass transport through the structure.

"Titania nanotube membrane" refers to a nanoporous membrane having an array of titania nanotubes on a titanium substrate where at least a portion of the titania nanotubes are open at both ends and capable of allowing mass transport from one side of the membrane to the other through the titania nanotubes.

"Fluid contact" refers to a location of two or more entities relative to each other in a manner that allows for fluid-phase mass transport between the entities.

"Quantity of gas" refers to an amount of material in the gaseous phase, wherein the material may include a single, substantially pure gas, or a mixture of multiple gases. A quantity of gas can include the total amount of gas in a reservoir.

"Water-soluble gas" refers to a gas that has a solubility in water at a temperature of 37° C. and a pressure of 1 atmosphere that is greater than the solubility of air in water at a temperature of 37° C. and a pressure of 1 atmosphere. The equilibrium solubility of air (oxygen and nitrogen combined) in water under these conditions is about 22 mg/liter (22 µg/mL). A water soluble gas (or mixture of gases) has a solubility of more than 22 mg/liter such as 23, 24, 25, 26, 27, 28, 29, 30, 31, 32, 33, 34, 35, 36, 37, 38, 39, 40 or more than 40 mg/liter. The quantity of gas can comprise a water-soluble gas.

"Zero-order rate of release" refers to the rate of release that is independent of concentration of the therapeutic agent in the reservoir.

"Subject" refers to animals such as mammals, including, but not limited to, primates (e.g., humans), cows, sheep, goats, horses, dogs, cats, rabbits, rats, mice and the like. In certain embodiments, the subject is a human.

"Therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, Pharmaceutical Dosage Forms (vols. 1 3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins). In sensitized cells, the therapeutically effective dose can often be lower than the conventional therapeutically effective dose for non sensitized cells.

"Molecular diameter" refers to the diameter of the sphere of gyration of a polymer, which is a physical measure of the size of a molecule, and is defined as two times the mass weighted average distance from the core of a molecule to each mass element in the molecule. Stokes diameter or hydrodynamic diameter reflects the dimension of a molecule plus its associated water molecules as it moves through an aqueous solution, and is defined as the radius of an equivalent hard sphere diffusing at the same rate as the molecule under observation.

The term "polymer" refers to any molecule composed of more than three monomeric subunits.

The term "distal" in reference to a medical device or part thereof generally refers to an orientation away from a medical user of the device and towards a subject or patient.

The term "proximal" in reference to a medical device or part thereof generally refers to an orientation towards a medical user of the device and away from a subject or patient.

The term "biodegradable" refers to the ability of a polymeric substance to degrade into lower molecular weight species when introduced into a biological environment.

The term "soluble" refers to the ability of a substance to dissolve into a solvent such as a biological fluid, without degrading into lower molecular weight species.

The term "humectant" refers to a substance that attracts water and may function to promote hydration and, in some cases, dissolution of a composition, such as a composition of a therapeutic agent. A humectant can be a solid, a liquid or a gas as well as combinations and mixtures of the foregoing. A humicant can be a water-soluble gas.

DETAILED DESCRIPTION OF THE INVENTION

The invention pertains to devices, methods and compositions for extended release of beneficial substances such as therapeutic agents, and to methods of treating patients in need of treatment with the therapeutic agents. In some embodiments of the invention, the devices are implantable devices having a capsule encapsulating a reservoir for containing one or more therapeutic agents. In some embodiments, the reservoir contains a formulation of the therapeutic agent or therapeutic agents in a solid state, as well as means to promote uptake of fluids, such as interstitial fluid, into the reservoir upon implantation of the device. In some embodiments, the means include a humectant. In some embodiments, the humectant comprises a quantity of gas with a solubility in water at 37° C. and 1 atmosphere that is greater than the solubility of air in water at 37° C. and 1 atmosphere. The humectant can be a water-soluble gas. In some embodiments, the means include a quantity of at least one gas, which gas has a solubility in water at 37° C. and 1 atmosphere that is greater than the solubility of air in water at 37° C. and 1 atmosphere. In other words, the gas has more solubility than 22 mg/L in water.

In some embodiments, the reservoir contains a quantity of gas, in which at least one gas is a water-soluble gas. The term water-soluble gas refers to a gas having a greater solubility in water at a temperature of 37° C. and a pressure of 1 atmosphere when compared to the solubility of air in water (i.e., the solubility of air in water under these conditions is about 22 mg/liter). In some embodiments, the reservoir contains a formulation that generates a water-soluble gas upon contact with water. In some embodiments, the device is packaged within a packaging system having a substantially gas-impermeable barrier shell and containing at least one water-soluble gas.

Air contains about 80% nitrogen and 20% oxygen. The solubility of nitrogen in water at 37° C. and at 0.8 atmosphere partial pressure is about 15 mg/liter. The solubility of oxygen in water at 37° C. and at 0.2 atmosphere partial pressure is about 7 mg/liter. Consequently, the total solubility of air in water under these conditions is about 22 mg/liter. In certain instances, when the humectant is a gas, the solubility of the gas in water is more than 22 mg/liter.

In some preferred embodiments, the formulation of the therapeutic agent in the reservoir is dry when the device is implanted in a subject and thereafter admixes with interstitial body fluids entering the reservoir for dissolution and hydration.

In some embodiments, the present invention provides a method for increasing the rate of hydration of a solid pharmaceutical composition or the uptake of interstitial fluid in an implantable capsule, by including a humectant to increase the gaseous solubility of the encapsulated environment relative to air, to thereby increase the rate of hydration of the solid pharmaceutical composition.

In some preferred embodiments, release of the beneficial substance(s) is extended over at least one month. In more preferred embodiments, the release is extended over at least three months, 4, 5, 6, 7, 8, 9, 10, 11, or at least 12 months.

In some embodiments, devices of the invention have a reservoir containing a composition of a therapeutic agent, and at least one membrane configured to achieve the extended-release by controlling the rate of release of the therapeutic agent from the reservoir. In some embodiments, the membrane controlling the rate of release of the therapeutic agent is at least one nanoporous membrane. In certain embodiments, there are two or more membranes in the device.

In some embodiments, the pores in the membranes are nanochannels, such as those disclosed in U.S. Pat. No. 8,480,637 incorporated herein by reference. In some embodiments, the pores in the membranes are nanotubes, such as those disclosed in U.S. Patent Application Pub. No. 2014/0371687 incorporated herein by reference.

In some embodiments, compositions of the invention are disposed within a reservoir of an extended-release dosage form controlled by a nanoporous membrane, wherein the nanoporous membrane is configured to achieve extended-release of the therapeutic agent from the reservoir of a device.

In some embodiments, the release rate of the therapeutic agent is controlled by matching the dimensions of the pores in the nanoporous membrane to the molecular dimensions or the hydrodynamic dimensions of the therapeutic agent.

In some embodiments, the smallest dimension of the pores is not more than 5 times a molecular dimension or hydrodynamic dimension of the therapeutic agent. In some embodiments, the smallest diameter of the pores is not more than 1, 2, 3, 4, 5, 6, 7, 8, 9, 10, 11, or 12 times a molecular dimension or hydrodynamic dimension of the therapeutic agent.

In some embodiments, compositions of the invention comprise a beneficial substance, such as a therapeutic agent and a stability enhancing agent for the beneficial substance, wherein the stability enhancing agent provides long-term stability through an extended-release mechanism of the stability enhancing agent (e.g., in the form of a substance with limited solubility or a biodegradable polymer), such as disclosed in PCT/US15/058449, incorporated herein by reference.

In some embodiments, more than one beneficial substance such as a therapeutic agent is contained within the reservoir. In some embodiments, more than one stability enhancing agent is contained within the reservoir.

In some embodiments, the therapeutic agent is a protein or peptide.

In some embodiments, suitable peptides include, but are not limited to, beta-glucocerobrosidase, interferon alpha, interferon beta, interferon gamma, agasidase alpha, agasidase beta, exenatide, octreotide, LHRH, LHRH analogs, calcitonin, nutropin/somatropin, factor VIII, aldesleukin, forigerimod, NP fusion proteins, IL-12, a melanocyte stimulating hormone, and bapineuzumab.

In some embodiments, the protein or peptide therapeutic agents are Glucagon-Like Peptide-1 receptor agonists also known as GLP-1 receptor agonists. In some embodiments, the GLP-1 receptor agonist is exenatide. In certain instances, exenatide has CAS No. 141732-76-5 and an empirical formula of $C_{184}H_{282}N_{50}O_{60}S$.

In preferred embodiments, the amount of exenatide can be from about 60 µg to about 50 mg, such as 100 µg, 200 µg, 300 µg, 400 µg, 500 µg, 600 µg, 700 µg, 800 µg, 900 µg, 1 mg, 10 mg, 20 mg, 30 mg, 40 mg, or 50 mg.

In preferred embodiments, the compositions are non-aqueous formulations, such as a dry powder formulations or suspensions of dry powders in a non-solvent liquid. Upon hydration, for instance, after implantation of the device comprising the composition at a desired location in the body of a subject, components of the formulation starts to dissolve after uptake of interstitial fluid and become available for diffusion through the nonporous membrane.

Uptake of aqueous fluids, such as interstitial fluid, into a reservoir holding a beneficial substance, such as a drug in a formulation, is frequently driven by the level of solubility or hygroscopicity of the formulation. Hygroscopic substances, including solids such as salts, sugars or sugar derivatives, as well as liquids such as hygroscopic solvents like polyethylene glycol are powerful water attractants, and will promote the uptake of water into the reservoir. Such hygroscopic substances are often referred to as "humectants," and are commonly used to promote hydration and water uptake into compositions, such as cosmetic or pharmaceutical compositions. Quite advantageously, in certain aspects, using a humectant as disclosed herein provides an increased rate of hydration of a beneficial substance.

Air, which is mostly oxygen and nitrogen, has a relatively low solubility in water and can actually be a barrier to water uptake. The presence of an air gap between a hygroscopic formulation inside a reservoir and an aqueous environment outside the reservoir can impede or substantially block the uptake of water into the reservoir for some period of time. Consequently, dissolution of a therapeutic agent and its release from the device may be impeded or substantially blocked for a period of time. In certain aspects, the present invention speeds up the uptake of water into the reservoir and mitigates against this water uptake barrier.

It should be understood that even gases like oxygen and nitrogen, although not classified as "water-soluble," in this disclosure have some level of solubility in aqueous media, and that, given enough time, compositions of therapeutic agents in reservoirs containing air instead of water-soluble gases according to the invention will hydrate. However, the time required for such hydration may not be medically acceptable. Embodiments of the invention allow for the time required for hydration or rehydration to be brought within medically acceptable limits. Since those limits may differ from one application to another, the extent to which a reservoir has to be filled with a water-soluble gas may depend on the specific application. In particular, the delay of drug release from a second implant, inserted after explantation of a first, depleted implant, a so-called "drug holiday," may determine the acceptability of the rate of hydration of a dosage form. For instance, for a drug with a wide therapeutic window, and an elimination half-life of 18 hours or more, a delay in release after implantation of a second dosage form of 2 days or more may be acceptable. For a drug with a narrow therapeutic window, and half-life of a few hours, a 12-24 hour delay may be the maximum acceptable range.

Some embodiments of the current invention aim to solve the problem of slow hydration by reducing the amount of air inside a reservoir to levels that do not pose significant barriers to water uptake and drug release. In some embodiments, the formulations are packed tightly enough in the reservoir that the remaining amount of air does not pose a significant barrier to water uptake and drug release.

In some embodiments, air inside the reservoir is replaced with a humectant such as a water-soluble substance. In some embodiments, the water-soluble substance is a water-soluble fluid, such as a water-soluble gas. Water-soluble gas in the context of this disclosure refers to a gas with a greater solubility in water than air at a temperature of 37° C. and a pressure of 1 atmosphere. Such a gas may not only eliminate the barrier effect of air, but may, in effect, act as a hygroscopic ingredient, promote uptake of water into the reservoir and therefore, in effect, act as a humectant. The use of gas(es) as a humectant is particularly useful in the present invention since essentially the entire weight of the water-soluble gas can be occupied by liquid attracted into the reservoir.

Many water-soluble gases exist, and suitable gases can be selected based on the requirements and capabilities of the particular application of the invention. Examples of commonly used medically acceptable water-soluble gases of the invention include carbon dioxide ($CO_2$) and nitrous oxide ($N_2O$) and argon (Ar).

In some embodiments, the present invention provide an implantable drug delivery device comprising a gas as a humectant, wherein the volume ratio of therapeutic agent to humectant is between 1 part of therapeutic agent to 99 parts of humectant to 99 parts of therapeutic agent and 1 part of humectant (1:99 to 99:1). In preferred embodiments, the invention provides an implantable drug delivery device comprising a gas as humectant, wherein the volume ratio of therapeutic agent to humectant is about 5:95; 10:90; 15:85; 20:80; 25:75; 30:70; 35:65; 40:60; 45:55; 50:50; 55:45; 60:40; 65:35; 70:30; 75:25; 80:20; 85:15; 90:10; or 95:5. In some embodiments, additional liquid or solid humectants can be present, in addition to a water-soluble gas.

In some embodiments of the invention, an implantable drug delivery device comprises an amount of a water-soluble gas. Some embodiments of the invention comprise a single, substantially pure gas. Some embodiments comprise a mixture of water-soluble gases, such as a mixture of $CO_2$ and nitrous oxide (i.e. $N_2O$). Some embodiments comprise a mixture of water-soluble gas or water-soluble gases and air. Some embodiments of the invention comprise a mixture of a water-soluble gas or water-soluble gases and one or more inert gases, such as nitrogen ($N_2$). Other suitable water soluble gases include, for example, helium (He), argon (Ar) and mixtures thereof. In certain aspects, as long as the water soluble gas is more soluble in water than air's solubility in water, it is suitable for use in the present invention.

The desired composition of a gas mixture inside the reservoir may be determined on a case-by-case basis. In general, embodiments of the invention provide substantial hydration and initiation of significant drug release within 48 hours of implantation of a device in a subject. Preferred embodiments provide substantial hydration and initiation of significant drug release within 36 hours of implantation of a device in a subject. More preferred embodiments provide substantial hydration and initiation of significant drug release within 24 hours of implantation of a device in a subject.

Most preferred embodiments provide substantial hydration and initiation of significant drug release within 12 hours of implantation of a device in a subject.

In some embodiments of the invention, a gas mixture inside a reservoir of a device (i.e., the internal gaseous environment) contains at least 10% by weight of a water-soluble gas or water-soluble gases and about 90% air. In preferred embodiments, a gas mixture inside a reservoir of a device contains at least 25% by weight of a water-soluble gas or water-soluble gases. In more preferred embodiments a gas mixture inside a reservoir of a device contains at least 50% by weight of a water-soluble gas or water-soluble gases. In most preferred embodiments, a gas mixture inside a reservoir of a device contains at least 90% by weight of a water-soluble gas or water-soluble gases. In some most preferred embodiments, the gas inside a reservoir is a substantially pure water-soluble gas. In certain aspects, the ratio of water-soluble gas:air is about 10:90; 20:80; 30:70; 40:60; 50:50; 60:40; 70:30; 80:20; or 90:10. Of course, the forgoing ratios can be applicable to two or more water-soluble gases. A skilled person can appreciate that when more than two water-soluble gases are used, the ratios of all the gases equals 100% of the internal gaseous environment.

In an exemplary embodiment, a device has a reservoir of 100 microliter. The reservoir contains 70 milligram of a formulation with a density of 1.1 gram/cm$^3$, so the formulation occupies a volume of about 64 microliter, leaving a volume of 36 microliter filled with a quantity of gas. In this example, the quantity of gas comprises 80% $CO_2$ and 20% air by weight. (air, in this example, is treated as a single gas). At 20° C. and 1 atmosphere, $CO_2$ has a density of 1.8 g/L and air has a density of 1.2 g/L. 1 gram of this mixture includes 0.8 g of $CO_2$ and 0.2 g of air, equal to 0.8/1.8 liter of $CO_2$ and 0.2/1.2 liter of air, for a total of 0.61 liter per gram. Therefore, the density of the mixture is 1/0.614=1.63 gram/liter or 1.64 microgram/microliter. The reservoir therefore contains 36×1.64 micrograms=58.7 micrograms of gas, 80% of which is $CO_2$ (46.7 microgram) and 20% is air (11.7 microgram).

Alternatively, expressed as volume percentages at atmospheric pressure, this equals 58.7/1.8=26.1 microliter of $CO_2$ and 11.7/1.2=9.8 microliter of air, or in volume percentages, 73% of $CO_2$ and 27% air. Of course, in the reservoir both $CO_2$ and air fill the entire 36 microliter volume, albeit at their respective partial pressures of 0.8 resp. 0.2 atmosphere.

In this context, the term "water-soluble" includes the dissolution behavior of a gas that reacts with other solutes in a solution. For instance, $CO_2$ reacts with water to form carbonic acid ($H_2CO_3$). At pH levels above the pKa (1) or pKa (2) of carbonic acid, the acid is ionized into bicarbonate ions ($HCO_3^-$) and carbonate ions ($CO_3^{2-}$), each of which are highly soluble in water. This makes $CO_2$ highly soluble in most body fluids, which typically have a pH just above 7.

Similarly, ammonia ($NH_3$) reacts with water to form $NH_4OH$. The solubility of ammonia can be enhanced by components creating a pH low enough to form salts of ammonia with free $NH_4^+$ ions in solution.

Many gaseous substances have sufficient solubility for application in the invention, including medical gases like $CO_2$ and $N_2O$, noble gases like argon (Ar) and more reactive or even toxic gases like $NH_3$, $H_2S$, HCl, $HNO_3$ and $Cl_2$. While for certain applications gases in the latter group may be acceptable, in practice a majority of preferred embodiments comprise medical gases, like $CO_2$ and $N_2O$, or an inert gas like Ar.

Some embodiments of the invention are particularly suitable for drug delivery devices having a reservoir and a membrane technology allowing for water uptake by convective flow, such as membranes with capillary channels, and micro- and nano-tubes. In particular, embodiments of the invention may be useful in combination with nanoporous membranes, including nanoporous membranes based on titania nanotubes.

In preferred embodiments, compositions of therapeutic agents in such devices are present in dry, solid form during shelf storage and at the time of implantation. Some devices of the invention rely on the uptake of interstitial fluid upon implantation to dissolve the compositions and render the therapeutic agent available for diffusion through the fluid-filled nanopores.

Ten 40 microliter titanium reservoirs were filled with a formulation containing 10 mg of powdered exenatide, 3.3 mg of powdered methionine and 5 mg of powdered PLGA. The reservoirs were sealed with titanium screw caps holding the nanoporous membranes.

Five systems received a purge with $CO_2$ as the last step of the system preparation just before immersion of the devices in phosphate buffered saline (PBS) as part of the test protocol.

The systems were hydrated by submersion with the membranes facing down into phosphate buffered saline (PBS) at pH 7.4 and 37° C. in 4 ml glass HPLC vials.

Buffer uptake was followed by weight measurements of the devices over time. Weight increases were corrected for adherent water on the outside of the systems by subtracting the average weight gain of control devices without porous membranes.

Release rates were measured by performing HPLC on the incubation solutions. The incubation solutions were refreshed at regular intervals to avoid complications due to excessive degradation of exenatide in the buffer.

FIG. 1 shows the delay in weight gain and fluid uptake in the air-filled systems compared to the $CO_2$ filled systems.

Figure 2:
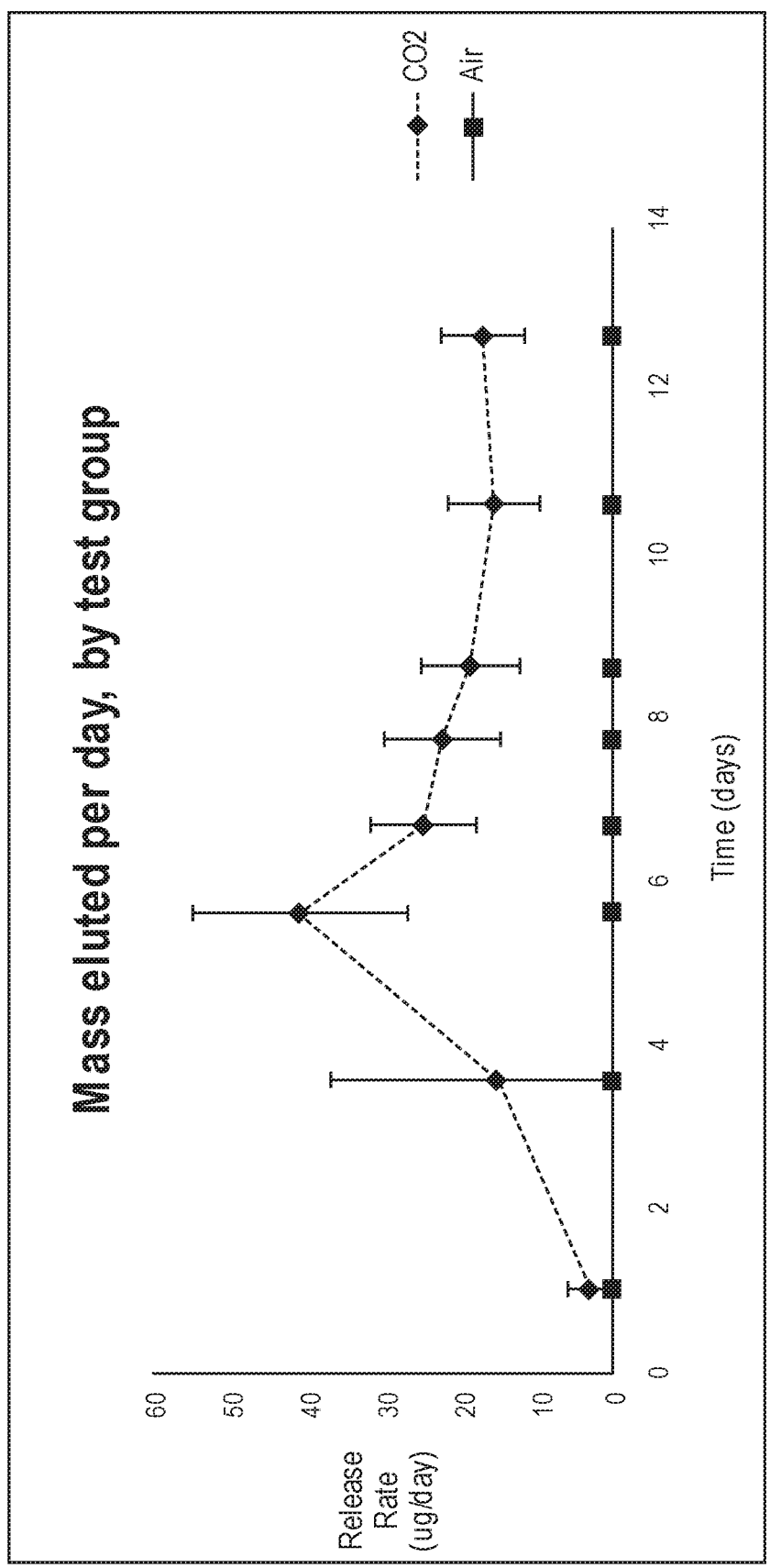
FIG. 2 illustrates the effect of an atmosphere of $CO_2$ vs. an atmosphere of air in the reservoir of a device on the start-up time of drug release from the device.

FIG. 2 shows the delay in measurable exenatide from the air-filled systems, with no measurable amount of exenatide being released up to day 13.

Without being bound by a particular theory, it is surmised that gases of the invention may facilitate the uptake of water through such nanotubes by any of a variety of mechanisms.

First, the solubility of the gases in body fluids will tend to draw interstitial fluid from the implant site into the nanotube membrane and into the reservoir of the device.

Gases of the invention, such as $CO_2$ and $N_2O$, having good solubility in interstitial fluid, will be able to dissolve in the fluid entering the reservoir and to diffuse out of the reservoir through the fluid-filled pores of the membrane.

Second, some embodiments of the invention employ nanoporous membranes having nanotubes with a hydrophilic surface. Such nanotubes may exhibit rapid water uptake through capillary action when brought into contact with an aqueous medium, like body fluids. Once filled with interstitial fluid, such tubes may become barriers for gases with a low solubility in water or interstitial fluid, like oxygen and nitrogen, since the process of dissolution and diffusion of these gases will be slow. Gases like $CO_2$, $N_2O$ and Ar, by contrast, will dissolve better and diffuse out more rapidly.

Third, some embodiments of the invention employ nanoporous membranes having nanotubes with hydrophobic surfaces. Wetting of those surfaces, i.e. the replacement of a nanotube-air interface with a nanotube-liquid interface may be extremely difficult, and in this case, penetration of interstitial fluid into the nanotubes may be significantly impaired. The presence of a water-soluble gas in the nanotubes solves this problem, since the water soluble gas dissolves in the interstitial fluid, thereby leading to a replacement of a nanotube-gas interface with a nanotube-fluid interface.

Fourth, interstitial fluid in a live subject may be more or less in equilibrium with air, and contains close to equilibrium amounts of nitrogen and oxygen. Nitrogen and oxygen, contained within reservoirs of the invention would have to dissolve in interstitial fluid coming into the device in order to diffuse out. However, the near-equilibrium concentrations of nitrogen and oxygen in the incoming interstitial fluid may impede the additional dissolution of air from the reservoir and hence its diffusion out of it. The presence of other gases that nitrogen and oxygen, such as $N_2O$, $CO_2$ or Ar in the reservoir may accelerate their dissolution and diffusion out of the reservoir, and, consequently, the uptake of interstitial fluid.

Some methods to manufacture embodiments of the invention include single or repeated cycles of evacuation and filling with a water-soluble gas of a reservoir in a device containing a formulation of a therapeutic agent.

For instance, an implantable device with a titania nanotube membrane according to U.S. Patent Application Pub. No. 2014/0371687 may have a reservoir of 250 microliters, containing 150 milligram of a formulation of a therapeutic agent, leaving a gas volume in the order of 100-150 microliters, depending on the density of the formulation. Even if the device were initially to contain pure air in addition to the formulation of the therapeutic agent, a single evacuation to 0.01 atmosphere and refilling with 100% $CO_2$ will reduce the air content inside the reservoir to 1%. Similarly, a cycle of evacuation to 0.1 atmosphere, refilling with 100% $N_2O$ and repeating the process once will create an atmosphere of 99% $N_2O$ and 1% air.

In certain instances, the device has a reservoir capacity with a volume of about 10 microliters to about 10 milliliters. In certain instances, the reservoir has a volume of about 10 to about 100 µl such as 10, 20, 25, 30, 35, 40, 45, 50, 55, 60, 70, 80, 90, or 100 µl. In other instances, the reservoir is about 25-60 µl or about 30-50 or even about 30-45 µl. In other instances, the reservoir is about 100-500 microliters, 150-450 microliters, or about 150-350 microliters, such as about 250 microliters.

In certain instances, the formulation is about 50 mg to about 400 mg, or about 100-300 mg, or about 150-250 mg. Further, there is a gas volume of about 50-500 microliters, or about 100-350 microliters, or 100-250 microliters depending on the density of the formulation.

Some methods of fabrication further improve the efficiency of the water-soluble gas filling cycle or cycles by admitting the water-soluble gas at a pressure above ambient atmospheric pressure, thus speeding up the uptake of water-soluble gas by the reservoir. Such embodiments are particularly useful in cases where evacuation and filling of reservoirs is throttled, for instance by the use of a membrane with capillary channels, or micro- or nano-tubes.

Other methods include performing the entire assembly of the device in a water-soluble gas environment.

Some embodiments of the invention include a formulation that generates a water-soluble gas in-situ. Examples of such formulations include mixtures of a solid form of a first acid and a solid form of a salt of a second acid, wherein the second acid can decompose into at least one gaseous decomposition product. Examples are salts of carbonic acid, which upon reaction with another acid decompose to form $CO_2$. Other examples include salts of nitrous acid, which can decompose into nitric oxide and nitrogen dioxide, and salts of sulfurous acid, which can decompose into sulfur dioxide.

For instance, a mixture of dry powders of sodium bicarbonate ($NaHCO_3$) and citric acid ($C_6H_8O_7$) will react to form $CO_2$ when in contact with water. A small amount of such a mixture can be included in a formulation inside a reservoir of a dosage form, in close proximity to a release rate controlling membrane. Even a small amount of water entering the reservoir through the rate controlling membrane will trigger a reaction between the sodium bicarbonate and the citric acid, resulting in the generation of $CO_2$.

In some embodiments of the invention, reservoirs of the devices contain a water-soluble gas, as well as a mixture of a solid form of a first acid and a solid form of a salt of a second acid, wherein the second acid can decompose into at least one gaseous decomposition product.

For instance, an implantable device with a titania nanotube membrane according to U.S. Patent Application Pub. No. 2014/0371687 may have a reservoir of 100 microliters, containing 70 milligram of a formulation of a therapeutic agent and about 30 microliter of $CO_2$ and a small amount of air. In addition to the formulation of the therapeutic agent, a mixture of 384 µg of citric acid and 168 µg of sodium bicarbonate may be included in the reservoir, adjacent to the nanotube membrane. Once a small amount of interstitial fluid has entered through the nanotubes, the reaction between the citric acid and sodium bicarbonate may produce 44 µl of $CO_2$ that will drive gas out of the device and the nanotubes, leave an atmosphere with a high $CO_2$ content, and subsequently facilitate the uptake of more interstitial fluid.

Some methods to manufacture embodiments of the invention include packaging a device having a reservoir containing a formulation of a therapeutic agent and a having a gas-permeable membrane under a large excess of the desired water-soluble gas in the commercial packaging.

Embodiments of the invention include systems comprising devices having a capsule encapsulating a reservoir containing a therapeutic agent and having at least one nanoporous membrane, wherein the devices are contained within the interior of a packaging system that comprises a substantially gas-impermeable barrier shell surrounding the interior and contains at least one water-soluble gas in the interior. Packaging systems with gas-impermeable barrier shells are well known in the art, including packaging of medical devices (Medical Device Packaging Handbook, Second Edition CRC Press, Aug. 25, 1998). Such packaging systems include, for instance, metalized, heat-sealed foil pouches, multilaminate polymeric pouches and packaging systems comprising a tray with a pealable lid, wherein the tray and the lid are manufactured from a substantially gas-impermeable material.

For instance, a system for extended-release of a therapeutic agent according to the invention comprises an implantable device with a titania nanotube membrane according to U.S. Patent Application Pub. No. 2014/0371687 having a reservoir of 50 microliters, the reservoir containing 35 milligram of a formulation of a therapeutic agent, leaving a gas volume in the order of 15-20 microliters, depending on the density of the formulation. The device may be packaged in a commercial package such as a heat-sealable metalized foil pouch, with an internal volume of 10 ml and filled with 100% medical grade $CO_2$. Gas exchange with the $CO_2$ in the package would provide an atmosphere with only 0.15 to 0.20% air in the reservoir. Packaging sensitive materials in an inert environment, like $N_2$, Ar and $CO_2$ gas is a well-developed technology that may be applied to embodiments of the invention using a water-soluble gas.

In some embodiments, a protective cap is applied to a device during manufacturing, on top of the capsule and over the nanoporous membrane, after filing the reservoirs with therapeutic agent and a water-soluble gas. In some embodiments, the cap is a removable cap, like a metal or polymeric cap. In some embodiments, the cap is a soluble or biodegradable cap, designed to dissolve or degrade after implantation of the device in a subject. In some embodiments such caps can be made of impermeable, rapidly soluble or biodegradable materials, like for instance a glassy composition of sugars or other carbohydrates, a soluble waxy substance like high molecular weight poly-ethylene glycol, or a soluble glassy substance like dry poly-vinylpyrrolidone. Protective caps may be applied to devices with a water-soluble gas inside the reservoirs at ambient or atmospheric pressure, but the invention is not so limited, and the caps may be applied with the water-soluble gas inside the reservoir at any desired pressure.

In some embodiments, an implantable drug delivery device containing a therapeutic agent and a water-soluble gas is contained within a hollow needle used for implantation of the device. The lumen of the needle may be filled with a water-soluble gas and capped with a removable cap on the sharpened distal end. The cap may be removed just before use.

Figure 3A:
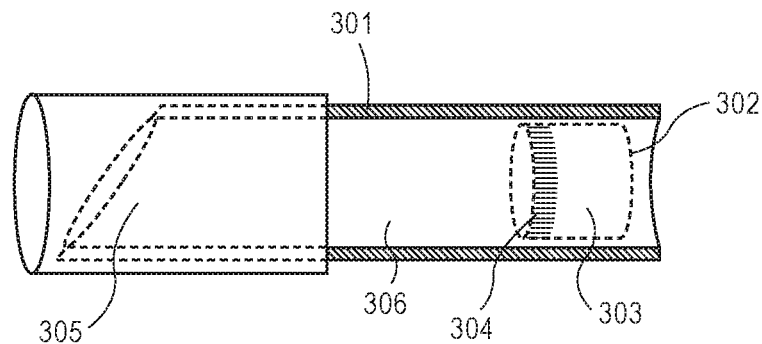
FIG. 3A illustrates a first embodiment of the invention with a drug delivery device contained within a hollow implantation needle.

As illustrated for an exemplary embodiment illustrated in FIG. 3A, hollow needle 301 may contain implantable device 302, having a reservoir 303 containing a therapeutic agent and a water-soluble gas, and having nanoporous membrane 304. Hollow needle 301 is capped with cap 305. In some embodiments, cap 305 is a substantially hermetically sealing cap. Lumen 306 of needle 301 contains a quantity of gas, including at least one water-soluble gas. During use of the device, cap 305 is removed from needle 301 just before implantation of the device, such that the water-soluble gas in lumen 306 reduces contamination of the water-soluble gas inside reservoir 303 with ambient air.

In some embodiments, an implantable drug delivery device containing a therapeutic agent and a water-soluble gas is contained within a hollow needle used for implantation of the device. The lumen of the needle may be filled with a water-soluble gas and a plug may be inserted into the needle, inhibiting the water-soluble gas from escaping. During implantation of the device, the plug may be expelled into the subcutaneous space together with the drug delivery device. In preferred embodiments, the plug is made of a soluble or biodegradable material.

Figure 3B:
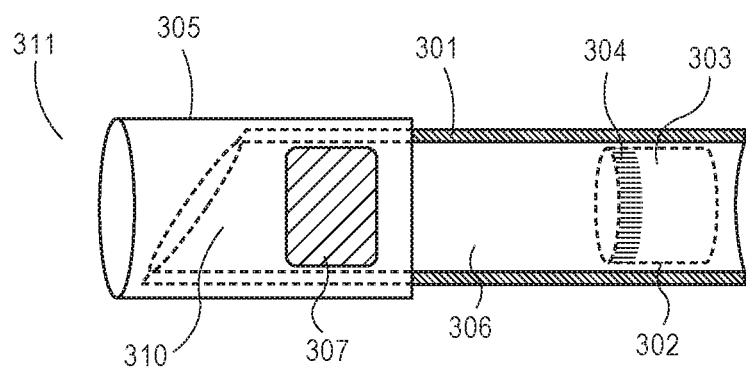
FIG. 3B illustrates a second embodiment of the invention with a drug delivery device contained within a hollow implantation needle.

As illustrated in an exemplary embodiment shown in FIG. 3B, plug 307 may be included in the device, and provides a barrier for the water-soluble gas in lumen 306 up until the moment of expulsion of device 302 from needle 301 in a site of implantation. Plug 307 is preferably manufactured out of a biocompatible material that is soluble or biodegradable, many of which have been described in the art of development and use of biomaterials. Typical examples include, but are not limited to, carbohydrates, a mono-, oligo- or polysaccharides, soluble synthetics such as poly-vinylprrolidone or poly-ethyleneoxide, or a biodegradable polymers such as a homopolymer or copolymer of lactic and glycolic acid. Optionally, cap 305 may be used on the embodiment.

In some embodiments, plug 307 is shaped to substantially fill lumen 310, thereby reducing the potential for air to enter lumen 310 and becoming trapped under the skin at the implant site.

During use of the device, cap 305 is removed, and needle 301 may be inserted under the skin of a subject, and device 302 may be expelled from needle 301, for instance by a plunger system (Not shown). Expulsion of device 302 will drive plug 307 out of the needle and into a subcutaneous space. Preferably, plug 307 will dissolve or bio-degrade over time in the subcutaneous space.

Figure 3C:
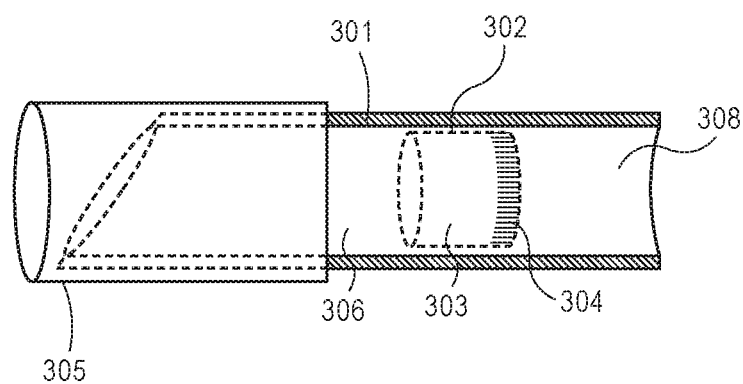
FIG. 3C illustrates a third embodiment of the invention with a drug delivery device contained within a hollow implantation needle.

As illustrated in yet another exemplary embodiment as shown in FIG. 3C, the orientation of device 302 inside needle 301 can be reversed, with membrane 304 facing away from cap 305. In this embodiment, lumen 308 may contain at least one water-soluble gas. Lumen 306, in addition, may optionally contain a water-soluble gas.

During use of the device cap 305 is removed and needle 301 may be inserted under the skin of a subject, and device 302 may be expelled from needle 301, for instance by a plunger system (Not shown). Because of the orientation of membrane 304, and the optional presence of a water-soluble gas in lumen 306, ambient air is substantially prevented from entering reservoir 303.

Figure 3D:
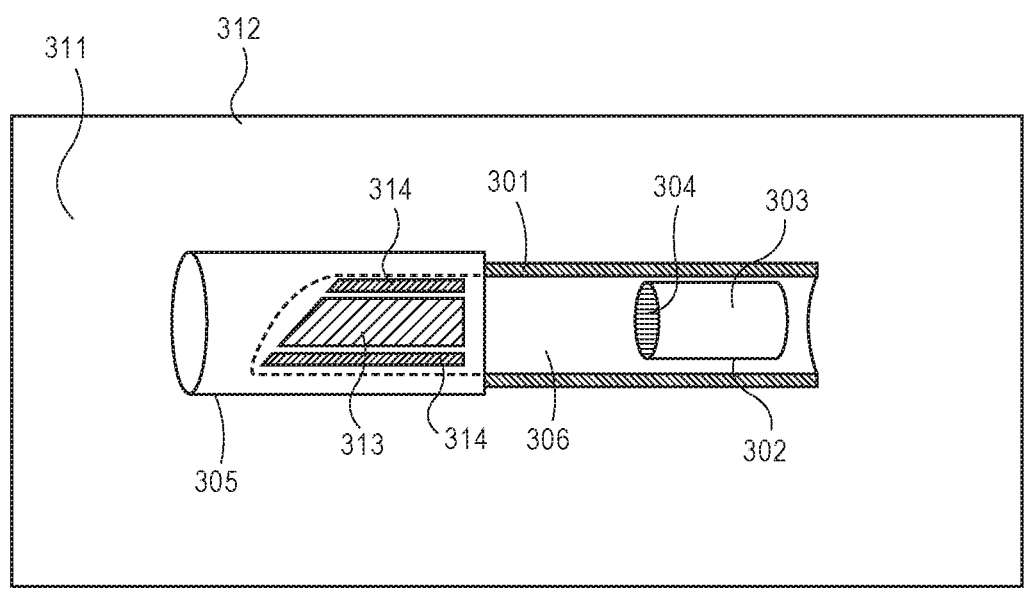
FIG. 3D illustrates an embodiment of the invention with a drug delivery device contained within a packaging system.

In some embodiments, as illustrated in FIG. 3D, plug 313 is a plug having one or more calibrated channels 314 allowing for restricted gas exchange between lumens 306 and interior 311 of a packaging system with a wall 312. In this example, plug 313 is shaped to substantially eliminate lumen 310 described in FIG. 3B. Lumen 306 may be in fluid contact with interior 311 of the packaging system, for instance through cap 305, wherein cap 305 allows fluid contact between lumen 306 and the interior 311 of the packaging system. In such embodiments, implantable device 302 may be loaded into needle 301 during manufacturing, plug 313 may be inserted into needle 301, and the system packaged inside a packaging system having a gas-impermeable barrier shell 312. The packaging system can be filled with a quantity of gas comprising at least one water-soluble gas. During storage of the system, gas exchange between lumen 306, reservoir 303 of the device and the interior 311 of the package will fill reservoir 303 with the desired gas composition, thereby avoiding a separate gas filling step during manufacturing and facilitating the manufacturing process. In contrast, since the calibrated channels on plug 313 restrict gas exchange over short periods of time, they prevent unwanted gas exchange between the reservoir 303 and the clinical environment during use of the device.

Embodiments of the invention include methods for treating subjects having type 2 diabetes with devices of the invention releasing exenatide. The effectiveness of such treatments can be measured by determining plasma levels of exenatide upon treatment, or by determining plasma levels of hemoglobin A1C (HbA1C) upon treatment.

The doses of exenatide suitable for the treatment of type 2 diabetes can provide any suitable mean steady-state plasma concentration of the therapeutic agent in the subject. For example, the mean steady state plasma concentration can be from 10 pg/ml to 10,000 ng/ml. In some embodiments, the mean steady state plasma concentration for exenatide can be from 170 pg/ml to 600 pg/ml. In some embodiments, the mean steady state plasma concentration for exenatide can be from 170 pg/ml to 350 pg/ml. In some embodiments, the mean steady state plasma concentration for exenatide can be from 170 pg/ml to 290 pg/ml.

The doses of exenatide suitable for the treatment of type 2 diabetes can provide any suitable steady state plasma concentration of HbA1C. For example, the steady state plasma concentration of HbA1C can be lower than 105, 9%, 8%, 7% or 6%. For example, the steady state plasma concentration of HbA1C can be lowered from baseline by at least 0.5%, at least 1%, at least 1.5% or at least 2%.

The embodiments described above are strictly exemplary embodiments. They are included for the sole purpose of illustrating the invention with examples, and are not to be interpreted as limitations on the entire scope of the invention as described in this disclosure.

What is claimed is:

1. An implantable drug delivery device, said device comprising:
    a capsule suitable for implantation;
    a reservoir encapsulated by the capsule;
    at least one nanoporous membrane in fluid contact with the reservoir;
    a therapeutic agent, which is hydrated in a body fluid; and
    a quantity of gas to promote hydration of the therapeutic agent in the body fluid, wherein the therapeutic agent and the quantity of gas are contained within the reservoir, and wherein the quantity of gas comprises one or more gases with a solubility in water at a temperature of 37° C. and a pressure of 1 atmosphere that is greater than the solubility of air in water at a temperature of 37° C. and a pressure of 1 atmosphere.

2. The implantable drug delivery device of claim 1, wherein the quantity of gas comprises at least 10% by weight of one or more gases with a solubility in water of more than 22 mg/liter at a temperature of 37° C. and a pressure of 1 atmosphere.

3. The implantable drug delivery device of claim 1, wherein the quantity of gas comprises at least 25% by weight of one or more gases with a solubility in water of more than 22 mg/liter at a temperature of 37° C. and a pressure of 1 atmosphere.

4. The implantable drug delivery device of claim 1, wherein the quantity of gas comprises at least 50% by weight of one or more gases with a solubility in water of more than 22 mg/liter at a temperature of 37° C. and a pressure of 1 atmosphere.

5. The implantable drug delivery device of claim 1, wherein the quantity of gas comprises at least 90% by weight of one or more gases with a solubility in water of more than 22 mg/liter at a temperature of 37° C. and a pressure of 1 atmosphere.

6. The implantable drug delivery device of claim 1, wherein the quantity of gas comprises a substantially pure gas with a solubility in water of more than 22 mg/liter at a temperature of 37° C. and a pressure of 1 atmosphere.

7. The implantable drug delivery device of claim 6, wherein at least one gas with a solubility in water of more than 22 mg/liter at a temperature of 37° C. and a pressure of 1 atmosphere is one of $CO_2$, $N_2O$ and Ar.

8. The implantable drug delivery device of claim 1, further comprising a cap located on the capsule over the nanoporous membrane.

9. The implantable drug delivery device of claim 8, wherein the cap forms a substantially hermetical seal over the nanoporous membrane.

10. The implantable drug delivery device of claim 9, wherein the cap is one of a biodegradable cap and a soluble cap.

11. The implantable drug delivery device of claim 1, wherein the at least one nanoporous membrane is a titania nanotube membrane.

12. The implantable drug delivery device of claim 1, wherein the at least one nanoporous membrane is configured to achieve extended release of the therapeutic agent.

13. The implantable drug delivery device of claim 1, wherein the therapeutic agent is a protein or peptide.

14. The implantable drug delivery device of claim 1, wherein peptide is a member selected from the group consisting of beta-glucocerobrosidase, interferon alpha, interferon beta, interferon gamma, agasidase alpha, agasidase beta, exenatide,
    octreotide, LHRH, LHRH analogs, calcitonin, nutropin/somatropin, factor VIII, aldesleukin, forigerimod, NP fusion proteins, IL-12, a melanocyte stimulating hormone, and bapineuzumab.

15. The implantable drug delivery device of claim 1, wherein the peptide is exenatide.

16. The implantable drug delivery device of claim 15, wherein the exenatide is present in an amount from about 60 µg to about 50 mg.

* * * * *